(12) United States Patent
Michaelis

(10) Patent No.: US 11,047,318 B2
(45) Date of Patent: Jun. 29, 2021

(54) FUEL TESTING DATA ACQUISITION SYSTEM CALIBRATOR AND SIGNAL SIMULATOR

(71) Applicant: Chad Alan Michaelis, Cresson, TX (US)

(72) Inventor: Chad Alan Michaelis, Cresson, TX (US)

( * ) Notice: Subject to any disclaimer, the term of this patent is extended or adjusted under 35 U.S.C. 154(b) by 0 days.

(21) Appl. No.: 17/251,805

(22) PCT Filed: Jun. 13, 2019

(86) PCT No.: PCT/US2019/037005
§ 371 (c)(1),
(2) Date: Dec. 13, 2020

(87) PCT Pub. No.: WO2019/241529
PCT Pub. Date: Dec. 19, 2019

(65) Prior Publication Data
US 2021/0115861 A1    Apr. 22, 2021

Related U.S. Application Data

(60) Provisional application No. 62/684,705, filed on Jun. 13, 2018.

(51) Int. Cl.
| F02D 35/02 | (2006.01) |
| G01N 33/28 | (2006.01) |
| F02D 41/00 | (2006.01) |
| F02D 41/30 | (2006.01) |
| F02D 41/22 | (2006.01) |

(52) U.S. Cl.
CPC ......... *F02D 35/028* (2013.01); *F02D 41/009* (2013.01); *F02D 41/222* (2013.01); *F02D 41/30* (2013.01); *G01N 33/2817* (2013.01); *G01N 33/2829* (2013.01); *F02D 2041/224* (2013.01); *F02D 2200/0611* (2013.01)

(58) Field of Classification Search
CPC .... F02D 35/028; F02D 41/222; F02D 41/009; F02D 41/30; F02D 2041/224; F02D 2200/0611; G01N 33/2817; G01N 33/2829
See application file for complete search history.

(56) References Cited

U.S. PATENT DOCUMENTS

| 2,269,760 | A | * | 1/1942 | Eldredge | G01L 23/223 336/20 |
| 3,575,039 | A | * | 4/1971 | Beal | G01N 33/2817 73/35.02 |

(Continued)

FOREIGN PATENT DOCUMENTS

WO    WO2016135532 A1    9/2016

*Primary Examiner* — Carl C Staubach
(74) *Attorney, Agent, or Firm* — Carrington, Coleman, Sloman & Blumemthal, L.L.P.

(57) ABSTRACT

A fuel quality rating testing system and related methodology. The system comprises a data acquisition system, comprising: (i) circuitry for receiving a time-varying signal from a pickup, the pickup for coupling to a test engine; and (ii) circuitry for determining a fuel rating in response to the time-varying signal. The fuel quality rating testing system also comprises a communications path coupled to the fuel quality rating testing system and a calibrator.

24 Claims, 6 Drawing Sheets

(56) References Cited

U.S. PATENT DOCUMENTS

| | | | |
|---|---|---|---|
| 7,529,616 B2* | 5/2009 | Bizub | G01N 33/2829 |
| | | | 701/114 |
| 9,803,565 B1 | 10/2017 | Ge et al. | |
| 9,823,233 B2* | 11/2017 | Michaelis | G01N 33/22 |
| 2009/0223485 A1* | 9/2009 | Hamedovic | F02D 41/0025 |
| | | | 123/435 |
| 2010/0168989 A1* | 7/2010 | Gao | F02D 41/2429 |
| | | | 701/110 |
| 2015/0120211 A1* | 4/2015 | Michaelis | G01N 33/22 |
| | | | 702/22 |
| 2015/0176513 A1* | 6/2015 | Lana | F02D 41/008 |
| | | | 123/406.48 |
| 2017/0299568 A1 | 10/2017 | Cochet et al. | |
| 2018/0073457 A1* | 3/2018 | Dudar | F02N 11/0814 |
| 2019/0249610 A1* | 8/2019 | Moik | F02D 41/28 |
| 2020/0326307 A1* | 10/2020 | Michaelis | G01L 27/005 |

* cited by examiner

FUEL TESTING DATA ACQUISITION SYSTEM CALIBRATOR AND SIGNAL SIMULATOR

TECHNICAL FIELD

Example embodiments relate to detonation or combustion pickup apparatus and systems, and their calibration, for measuring octane or cetane.

BACKGROUND ART

The process of measuring fuel rating by octane or cetane, such as those prescribed in several ASTM standards, requires the use of a detonation pickup. The octane detonation (or combustion, for cetane) pickup produces an electrical signal representing one or more combustion characteristics. The pickup typically is used to sense pressure or vibration resulting from changes within the combustion chamber of a test engine. A typical pickup is exposed to elevated temperatures and vibration that may result in pickup degradation or failure. Indeed, blending fuels to an exact level is an expensive process, and the pickup is at the fuel testing signal chain's heart. There are many costs associated with a low or inaccurately performing pickup. One pickup's inferior performance can be a large cost driver in the fuel blending process. These costs can be greatly compounded over a testing fleet. An erroneous signal or failure of the pickup may be costly to trouble shoot or to correct an incorrectly measured value.

By way of further introduction, in addition to the detonation/combustion pickup, octane and cetane determinations are further determined by an electronic data acquisition system (DAS) that receives analog signals from the detonation pickup, typically through a signal chain with various interfaces. For example, the signal chain may contain several physical interconnections and cables prior to entering the analog input of the data acquisition system. Once the signal has entered into the data acquisition system, a logic device such as a personal computer or the like, will perform algorithms to develop a numerical equivalence to a known octane or cetane reference. The determinations of an octane number or cetane number are typically performed following a prescribed ASTM standard, such as the D2699, D2700, D2885 and D613. However, the signal chain to, and the data acquisition itself, are subject to signal degradation or error. Further, each engine has variances associated with the many mechanical parts that make up the running test engine. These variances introduce noise and instability to the test readings acquired by the data acquisition system, and as such detract from the ultimate precision of the test operation. Due to noise in the system, and machine to machine differences, a true machine precision determination is done by statistical analysis and not directly measured. The present inventor also has recognized the drawbacks of this approach as well, and example embodiments, therefore, seek to improve upon the prior art. Such example embodiments are also explored later in this document.

DISCLOSURE OF INVENTION

In one invention, there is provided a fuel quality rating testing system, comprising a data acquisition system with: (i) circuitry for receiving a time-varying signal from a pickup, the pickup for coupling to a test engine; and (ii) circuitry for determining a fuel rating in response to the time-varying signal. The fuel quality rating testing system also has a communications path coupled to the fuel quality rating testing system and a calibrator. The calibrator is coupled to the communications path, for outputting an alternative time-varying signal without requiring a running test engine to concurrently couple a signal to the calibrator. The circuitry for receiving receives the alternative time-varying signal, and the circuitry for determining determines a fuel rating in response to the alternative time-varying signal.

DETAILED DESCRIPTION OF THE INVENTION

Figure 1:
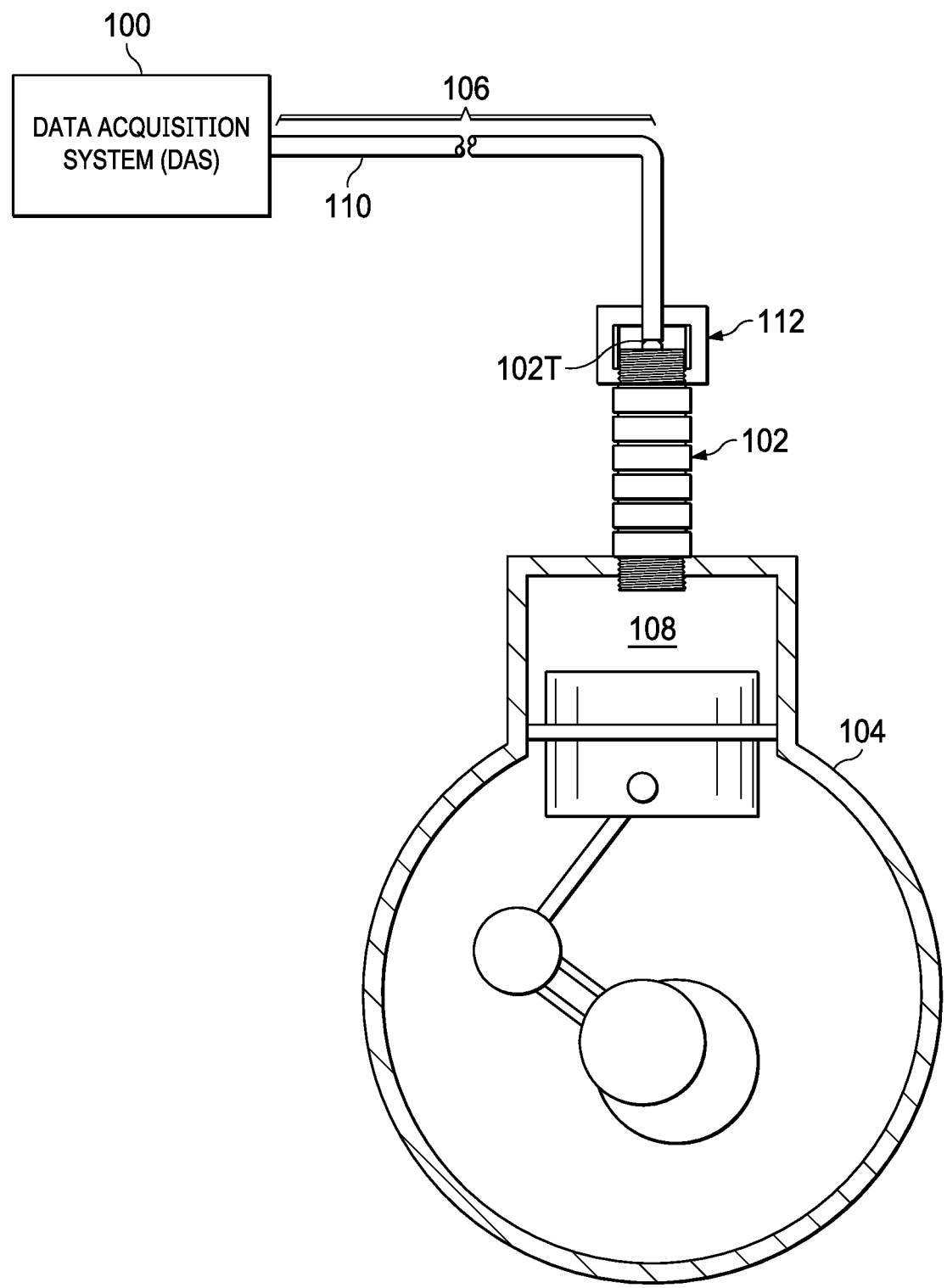
FIG. 1 illustrates a prior art environment including an octane/cetane data acquisition system (DAS) in connection with a detonation (or combustion) pickup still affixed to a test engine.

In various preferred embodiments, novel data acquisition calibrators are provided that in a preferred embodiment method may help octane or cetane testing managers and technicians achieve a higher resolution octane number or cetane number by a fuel quality rating data acquisition system. Particularly, FIG. 1 illustrates a prior art environment, including an octane/cetane rating data acquisition system ("DAS") 100, for example, for receiving time-varying signals from a pickup 102 that is connected to (e.g., threadbly into a cylinder head of) a test engine 104. Pickup 102 is configured and operable to detect a combustion event, for example as detonation in a gas test engine or ignition/combustion in a diesel test engine. Detonation pickups such as those described in U.S. Pat. No. 2,269,760 "Detonation Indicator" are an example of a type of detonation pickup that would benefit from the inventive scope, among others. Other types of pressure and vibration detonation pickups, used in measuring octane or cetane, also may benefit from the apparatus. In any event, the DAS 100 is connected by a communications path 106 to pickup 102.

In the prior art, the test engine 104 is run with a fuel of either known (as a reference) or unknown (being tested) octane/cetane, and conditions are imposed on the test engine 104 to force a knock event (for gas, or combustion or ignition for diesel) during the engine's combustion cycle. The pickup 102 couples to the test engine (e.g., by a fluid communication path of the engine cylinder head to a combustion chamber 108) and generates a time-varying signal in response to the combustion event. Ideally, for an octane evaluation, the time-varying signal has a peak that corresponds to the knock event, and the signal is coupled to the DAS 100 which detects that peak. Alternatively, as described in co-owned U.S. Pat. No. 9,823,233, issued Nov. 21, 2017, and entitled DETERMINING THE KNOCK RATING OF LIQUID SPARK-IGNITION ENGINE FUELS, which is hereby fully incorporated herein by reference, the DAS 100 may detect multiple attributes of the time-varying signal that occurs over a period of time during which the knock event occurs. The DAS 100 may include diverse types of analog or analog-to-digital DAS devices, as well as computational structures (e.g., central processing unit), associated with octane or cetane number measurement systems, and in any event from peak or ignition/combustion detection determines a fuel quality measure, such as an expressing fuel quality in an octane or cetane number. The ASTM standards reference the use of analog knock meters, digital knock meters, cetane meters, and computational (e.g., personal computer PC) based data acquisition systems. The path 106 may include a cable 110 as well as physical/ electrical interfaces, including for example a screw-on coupler 112 that physically attaches the cable 110 to threads on the pickup 102, while concurrently ensuring an electrical connection between the pickup 102 terminal(s) 102T and the conductor(s) of the cable 110. However, octane/cetane testing engines in the prior art have a varied level of repeatability from combustion event to combustion event. The variability of the test engine operation, therefore, and the entirety of the path 106, as well as the condition of pickup 102, may affect the determination of octane/cetane accuracy. Still further, the precision of measurement is figured by statistical methods and will vary in large fleets, from machine to machine, and from laboratory to laboratory.

In preferred embodiments, the system of FIG. 1 is modified to include a data acquisition calibrator apparatus and also optionally a methodology which, as an alternative to receiving a pickup time-varying signal from a running test engine, couple a known (and therefore usable for calibrating) time-varying calibration signal to path 106 to facilitate, for example, a common zeroing point in the octane/cetane DAS 100. Such an adjustment may help determine a higher resolution of measurement. Particularly, a data acquisition calibrator may be helpful in creating a known reference point in which to calibrate the DAS 100 at a determined zeroing floor for the fleet testing engines. In other words, an apparatus and method to determine correctly a precision determination may offer managers and technicians a means to calibrate (either initially or in a subsequent re-calibration) an octane or cetane testing system. The data acquisition calibrator also may be used to help diagnose noisy connections and faulty analog input electronics. Specifically and as detailed below, different preferred embodiment calibrators are provided, each of which mimic an operating test engine by generating a time-varying signal of known amplitude over time, repeatedly, to create a known calibration signal, that is, a noise free representation of a knock event or combustion event with an analog signal for the DAS 100 to consume and evaluate. Thus, with a known calibration signal, a calibration or zeroing measure (e.g., octane or cetane) reading can be performed by the DAS 100 in response to the known calibration signal, such that a later deviation from that calibration or zeroing measure, when taken again in response to the same known calibration signal, will indicate a change in the communications path 106, for example, in frequency response/impedance. Each such apparatus and method, therefore, allows a user to understand and account for system and signal noise that are encountered during a normal testing procedure. An example embodiment apparatus is sufficiently straightforward in use so that an example embodiment calibration method may be conducted prior to each fuel test to zero the fuel testing DAS. The example embodiment calibration apparatus and methodology will help users to identify biases in their octane and cetane measurement systems. This new level of bias detection will allow users to generate a more accurate fuel rating determination, which will result in substantial cost savings.

Figure 2:
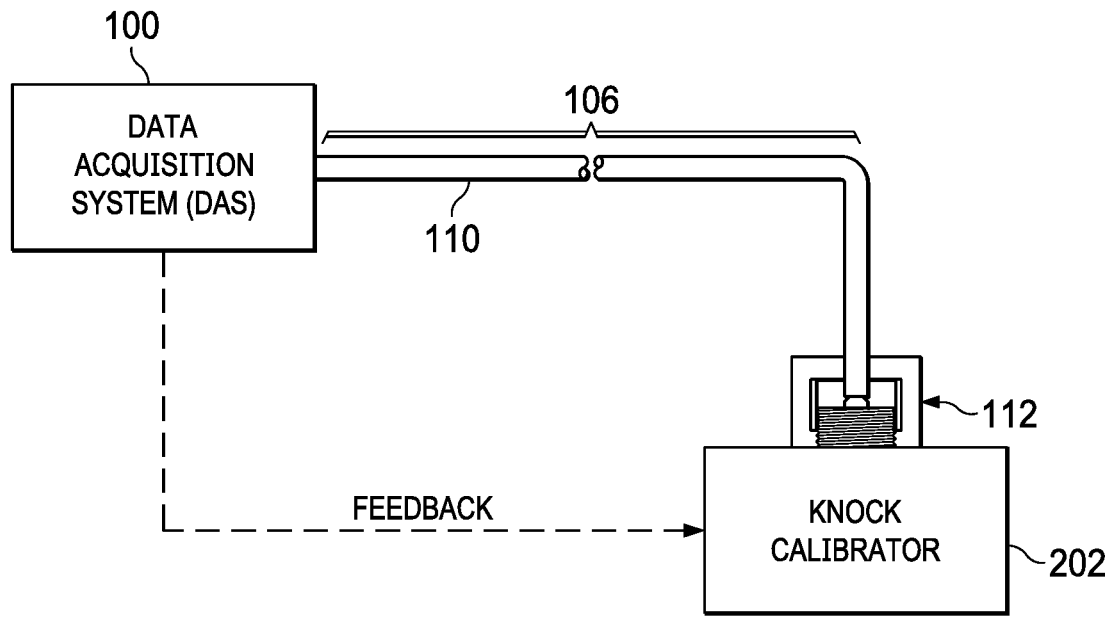
FIG. 2 illustrates a DAS and communications path coupled to a preferred embodiment detonation/ignition calibrator.

FIG. 2 illustrates the DAS 100 and the communications path 106, coupled to a preferred embodiment detonation/ignition calibrator 202. In an example embodiment, the calibrator 202 serves as the above-introduced data acquisition calibrator, which provides a known time-varying calibration signal, without requiring a concurrent running of the test engine 102. Specifically, the calibrator 202 is operable to output different time-varying signals, each with an appropriate time-varying amplitude and duration, to mimic an engine knock or combustion event were the test engine 104 running or with a running test engine connected, through a pickup, to the DAS 100. Moreover, the calibrator 202 may output time-varying signals of respective differing amplitudes (or profiles over time), so as to simulate fuels with different combustion characteristics associated with octane and cetane. As detailed below, different alternatives are contemplated for enabling the calibrator 202, including, for example, either a signal generator (see, FIG. 3) or for example a device (see, FIG. 4), other than the test engine, coupled to the pickup 102 so as to cause a response from the pickup 102 while it is coupled to the DAS 100, where each example provides a repeatable known calibration signal to the path 106 and to the DAS 100. Accordingly, the calibrator 202 may be considered, at a basic level, apparatus to generate or induce a representative signal through the path 106 and into DAS 100, where the signal mimics an output of a prior art pickup 102 attached to the test engine 104 when it is running. For example, the calibrator 202 may output a signal with a source impedance to mimic that of a pickup at running temperature, approximately 650 ohms DC resistance. The output signal is thereafter used in the process of octane or cetane number determination or calibration thereof. In any event, a considerable benefit of the FIG. 2 embodiment is resources (time, fuel, and the like) are not needed or wasted in running a testing engine while calibrating the DAS 100, and also in the repeatability of a calibration signal, as further detailed below. Moreover, the repeatability of the time-varying signal of the calibrator 202 is achieved without movable and/or mechanical parts. Thus, certain attributes of preferred embodiments may be contrasted, for example, to the embodiments of co-owned WIPO international publication number WO 2019/070690, entitled DETONATION PICKUP TESTER AND METHODOLOGY, published 11 Apr. 2019, and which is hereby fully incorporated herein by reference.

Completing FIG. 2, also shown is an optional feedback back from the DAS 100 to the calibrator 202. This feedback may be used for various purposes. As one example detailed later, the DAS 100 may enable the calibrator 202 to emit calibration time-varying signals. As another example detailed later, the DAS 100 may determine an error in its evaluation of octane/cetane measures, in response to calibrations signals received from the calibrator 202. In such an instance, the feedback may be used for error correction, for example to adjust one or more attributes of the calibrator, thereby influencing subsequent calibration signals.

Figure 3:
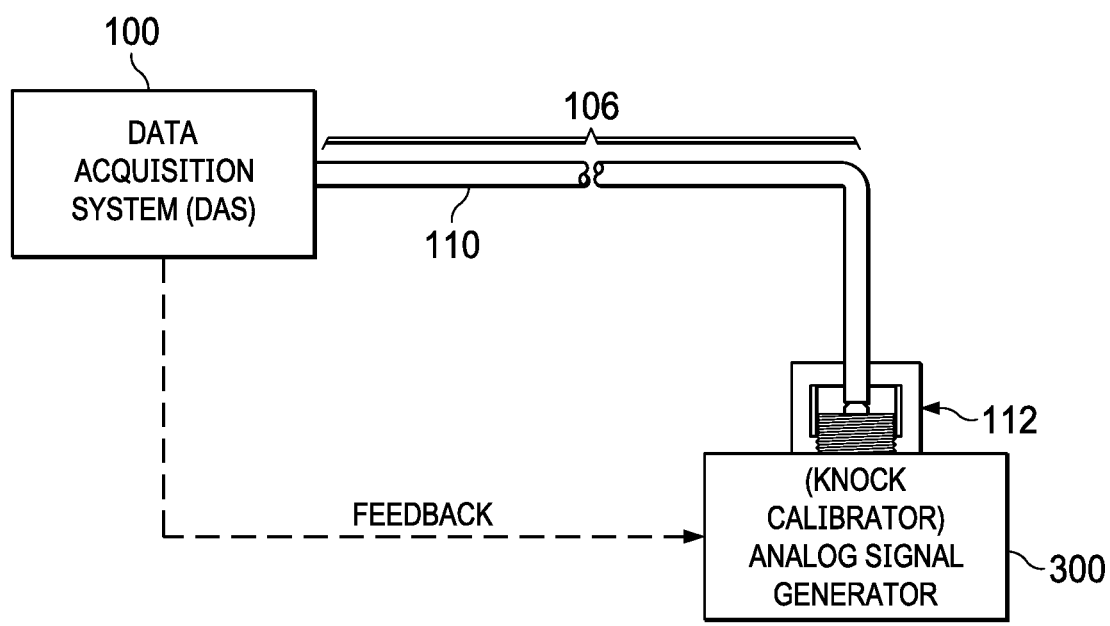
FIG. 3 illustrates the system of FIG. 2, where the detonation/ignition calibrator is implemented as an analog signal generator.

FIG. 3 illustrates the system of FIG. 2, where the detonation/ignition calibrator 202 thereof is implemented as an analog signal generator 300. The generator 300 is connected to the path 106, preferably using mechanical and electrical interfaces that are substantially similar or identical to those that couple to the pickup 102, where for example FIG. 3 again illustrates screw-on coupler 112 as an attachment mechanism between the cable 110 and the generator 300.

The generator 300 is implemented with appropriate circuitry to record and output, or recreate, output signals simulating an output of a prior art pickup 102 under various conditions. For example, the generator 300 may store (e.g., in digital storage) digitized time and amplitude varying electrical signal representations of actual engine cylinder pressure, and also be operable to output analog counterparts to the stored digital representations. Such counterpart signals, for example, may correspond to a low octane/cetane test fuel, a high octane/cetane test fuel, and an unknown octane/cetane test fuel having a fuel quality rating (octane or cetane) between the low and high, such as halfway between the low and high. In this manner, the generator 300 replaces the pickup 102 as an output source, and the generator 300 selectively outputs among stored simulated pickup analog time-varying signals, where each signal mimics a pickup response to an actual knock or combustion event. The output of the generator 300 therefore provides a repeatable signal to the path 106 and the DAS 100, and it leaves as much of the communications path the same as when that path is connected to the pickup 102, so as not to change the response of the system other than as it relates to the signal provided by the generator 300. As described below, therefore, the DAS 100 can receive, consume, and process the signal for calibration purposes.

Figure 4:
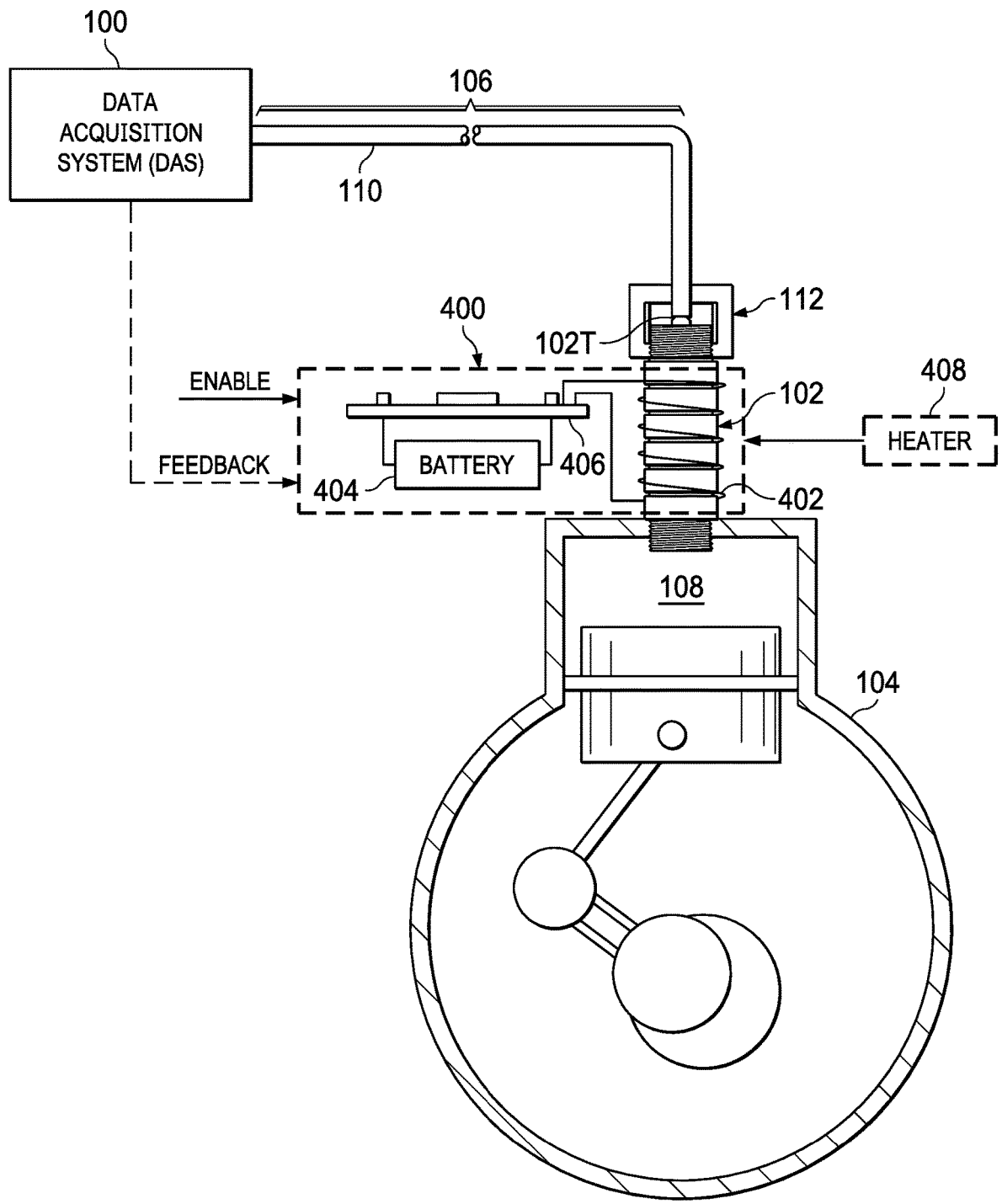
FIG. 4 illustrates the system of FIG. 2, where the detonation/ignition calibrator is implemented as a pickup signal inducer in combination with a detonation (or combustion) pickup.

FIG. 4 illustrates the system of FIG. 2, where the detonation/ignition calibrator 202 thereof is implemented as a pickup signal inducer 400, or as may be understood as the inducer 400 in combination with the pickup 102. In a preferred embodiment, the inducer 400 includes a coil 402 that fits around the outer perimeter of at least a portion of the pickup 102. Accordingly, in such an embodiment, one approach is to disconnect the screw-on coupler 112 from the pickup 102 so as to have access to the top thereof, and then to locate the inducer 400 so that its coil 402 surrounds a portion of the body of the pickup 102, as shown in FIG. 4, after which the screw-on coupler 112 is re-attached to restore the connection of the cable 110 to the pickup 102. In this regard, the inducer 400 also may include additional positional or fitment structure (not explicitly shown) so as to affix its coil in a desired orientation relative to the body of the pickup 102, such as with the coil concentrically encircling some or all of the pickup body. Note also that FIG. 4 also illustrates the pickup 102 while the pickup 102 is still installed in the test engine 104, which for example or convenience may be the case in some implementations, so as to allow the pickup 102 to be otherwise undisturbed from its typical location. In other implementations, however, the inducer 400 may be positioned relative to the pickup 102, while the pickup 102 is not installed in the test engine 104.

Looking in addition detail to the inducer 400, it further includes a power source (e.g., battery) 404 and a circuit board (e.g., PCB) 406, where the circuit board 406 includes necessary structure to generate and drive a signal to the coil 402, in response to assertion of an ENABLE signal, which may be manually or electronically controlled. In operation, therefore, the circuit board 406 applies a signal(s) to the coil 402, and the coil 402 responds by producing a magnetic field proximate the pickup 102. As known in the art, a pickup 102 may include inner pickup coils. Hence, the magnetic field produced by the coil 402 inductively couples energy onto the inner pickup coils, which causes a time-varying output signal at the terminal 102T. Indeed, note further that the calibrator approach of FIG. 4 further includes the pickup itself as part of the analyzed signal path, whereas the FIG. 3 approach does not. Further, apart from calibration, note that this same inductive coupling also may be used to test for resistance and continuity in combination with principles described in the above-referenced and incorporated co-owned WIPO international publication number WO 2019/070690. In any event, the coil 402 provides the ability to induce a pickup response, for example by alternating the polarized magnetic field, so as to create a corresponding time-varying signal, and which can be repeated with different energizing signals so that the pickup 102 responsively produces respective different time-varying signals. As detailed below, the DAS 100 is then operated to sense each electrical signal generated at the pickup's electrical terminal 102T (or plural such terminals), again for example so as to mimic an actual knock or combustion event corresponding to a particular octane/cetane level. Thus, alternative embodiments facilitate the use of the inducer 400 for a pickup, whether the pickup is suitable for either of octane or cetane measurements.

Lastly in connection with FIG. 4, an additional optional aspect is to include a heater 408, so as to couple heat energy into the pickup 102. In this manner, the pickup 102 may be heated above room temperature, for example to further work in combination with the induction stimulus applied by the inducer 400. In this way, the pickup 102 may be operated to simulate an environment akin to when the pickup is instead coupled to a running test engine 104. The heater 408 may be implemented in various manners. In one contemplated approach, the heater 408 is included within the form factor of the inducer 400. For example, heating elements may be added that also align around the body of the pickup 102 at the same time that coil 402 is aligned as shown. Indeed, in one additional aspect of such an embodiment, a separate coil (not shown) may be positioned (e.g., approximately concentrically) around some or all of the body of the pickup 102, where current is passed through the second coil to generate heat; in such an approach, for example, the second coil may have lower gauge wire and/or fewer windings as compared to the coil 402, so that the second coil is more readily used for higher power induction or resistive heat generation rather than low power signal generating magnetic induction. In such an endeavor, one skilled in the art will further be informed by these teachings to account for certain effects as between such a second coil and the coil 402, such as any noise generation, heat transfer, or interleaved/alternative operation of each coil so as to avoid or mitigate any possible interference in the induced signal provided to the path 106.

Figure 5:
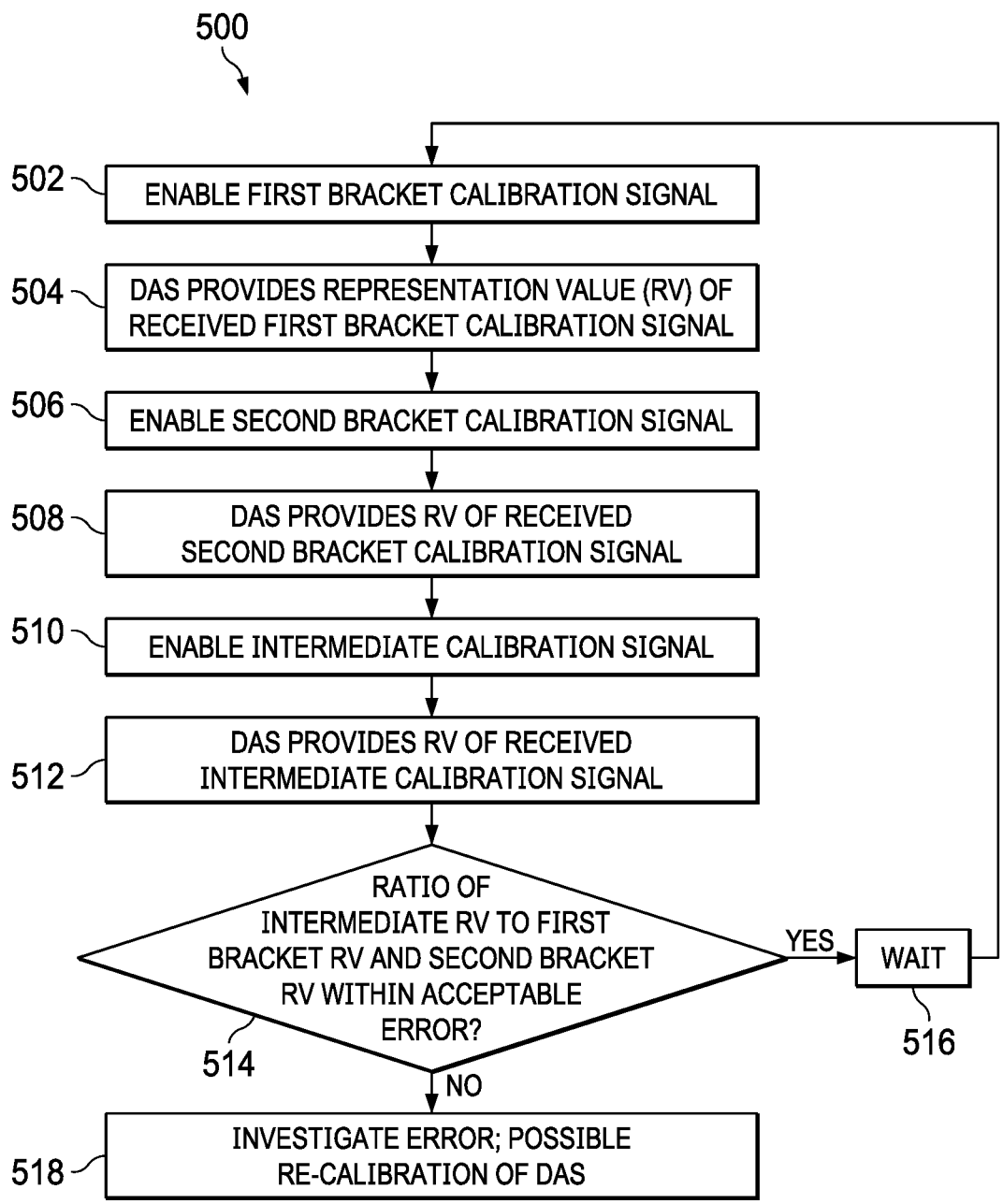
FIG. 5 illustrates a flowchart of a preferred embodiment method of operating a detonation/ignition calibrator in combination with operation of a DAS.

FIG. 5 illustrates a flowchart of a preferred embodiment method 500 of operating the detonation/ignition calibrator 202 (by example of the generator 300 of FIG. 3 or the inducer 400 of FIG. 4) in combination with operation of the DAS 100. Note that steps of the method 500 may be added as additional functionality to the DAS 100, or may be controlled/sequenced by additional apparatus. Particular implementation details, including re-arranging order, adding additional, or removing steps, are ascertainable by one skilled in the art given the teachings of this document.

In step 502 a user, or separate electrical controller (which may be part of, or in communication with, the DAS 100), operates the calibrator 202 to provide a first bracket calibration signal. For example, user control can be by way of a physical or graphical interface button, further optionally providing the user the ability to select which amplitude or time delay signal form will be provided by the calibrator 202. As detailed above, this calibration signal, and all others of method 500, are each an analog signal having a known time varying amplitude over a known duration. The signal is referred to herein as a bracket symbol for correspondence with what is used in the prior art with a running test engine, where a first known octane fuel is provided to the running test engine under varying conditions (e.g., by adjusting air-to-fuel ratio (AFR)), where under those conditions the pickup outputs a respective first reference (or set of) analog time varying signal in response to the test engine combustion cycle operating with the first known octane fuel. In the present embodiment, however, the calibrator 202 produces a simulated output signal, analogous therefore to a first octane fuel, but instead of requiring running of a test engine, the provided signal is either a stored signal in the signal generator 300 of FIG. 4, or it is a signal from the pickup 112 of FIG. 5 created in response to an appropriate stimulus from the inducer 400. Additionally, enabling the calibrator 202 may be modified to cause the calibrator 202 to successively repeat the same calibration signal, as typically the DAS 100 may anticipate receiving and analyzing (e.g., averaging) a number of signal samples over a period of time. Next, the method 500 continues from step 502 to step 504.

In step 504, the known calibration signal passes travels through the path 106 (i.e., the physical connection media) and into the DAS 100. The DAS 100 captures (e.g., sample and store) a time-varying signal response to the first bracket calibration signal, measures it, and evaluates it so as to provide a first bracket representation value (RV) of the signal, with the RV corresponding to an octane/cetane measurement of the first bracket calibration signal. Note that the RV may be determined by the DAS 100 according to different techniques. As one example, the DAS 100 identifies the peak value of the duration when the signal is greater than zero (or some threshold) and from that peak an RV of the octane/cetane measure is determined. As another example, and as detailed in the above-referenced and incorporated U.S. Pat. No. 9,823,233, an octane measure may be determined from at least two different waveform attributes of the captured time-varying signal. In any event, the first bracket RV also may be converted to a displayable image, such as a point (or trace, for example from multiple received signal, either at a same simulated AFR or for different simulated AFRs) on a screen, that is either connected to or part of the DAS 100, with the indication representing a determined octane/cetane level from the first bracket calibration signal. Next, the method 500 continues from step 504 to step 506.

Step 506, and the step 508 following it, repeat the same operations as steps 502 and 504, respectively, but here for a second bracket calibration signal and to determine its respective second bracket RV. Accordingly, if step 502 enables a first bracket calibration signal corresponding to a low octane test fuel, then conversely step 506 enables a second bracket calibration signal corresponding to a high octane test fuel (or vice versa). And, then in step 508, the DAS 100 samples, measures, and determines a second bracket RV for the second bracket calibration signal, which again may be depicted or indicated, for example as a point/plot on a screen. Next, the method 500 continues from step 508 to step 510.

Step 510, and the step 512 following it, repeat the same operations as steps 502 and 504 (or steps 506 and 508), respectively, but here for what is referred to as an intermediate calibration signal, the intermediate calibration signal presenting an amplitude between the first bracket calibration signal of step 502 and the second bracket calibration signal of step 506. In one example, the step 510 intermediate signal has a peak (or other measure attribute(s)) that is halfway between the first and second brackets provided by steps 502 and 506. Accordingly, when the step 510 signal is sampled and measured in step 512 by the DAS 100, then ideally the step 512 intermediate RV will be halfway between the RV of step 504 and the RV of step 508. Next, the method 500 continues from step 512 to step 514.

Step 514 determines if there is an error between the step 512 intermediate RV and what would be an expected value from the DAS 100, given the intermediate ratio of the step 510 intermediate calibrating signal between the step 502 first bracket calibration signal and the step 504 second bracket calibration signal. Continuing the prior example, if the intermediate calibration signal is halfway between the first and second bracket calibration signals, then step 512 should provide the step 512 intermediate RV as halfway between the step 504 first bracket RV and the step 508 second bracket RV, or at least within some acceptable error of halfway between the two. Or, if the step 510 intermediate calibration signal is some other fraction between the bracket calibration signals, then its respective intermediate RV should be the same fraction between the bracket RVs (or, again, within the step 514 threshold). An analogy that may apply, by way of illustrating the scope to one skilled in the art but without prejudice or admission of prior art, is the use of a high precision resistor to calibrate an ohm meter's measured value. In that case, the resistor is connected to the meter with an expectation that the meter will indicate a value equal to the known resistance of the high precision resistor. However, note that such a test is for a single resistance value. Using the same analogy, the current practice for testing an octane/cetane data acquisition system is to use long running statistical calculations to try and predict measurement biases. This would be like testing many resistors and using statistical analysis to determine the ohm meter's precision or bias, and requires historic data to be kept and draws certain inferences from continuity of data while relying on an input that comes directly from the pickup in response to operating with the test engine. Hence, the statistical method is very time consuming and more error prone than using a high precision reference. In contrast, and returning to a preferred embodiment, the method 500 uses three calibration signals to evaluate the expected ratio of the intermediate signal RV relative to the bracket RVs, with the relative ratio of the simulated calibration signals known. Thus, if the DAS 100 (including its hardware and software) and its related path 106 are properly functioning, the intermediate RV should evaluate at the same fractional relationship between the bracket RVs to match (within a determined acceptable error) the fractional relationship between the intermediate calibration signal as to the bracket calibration signals. Step 514, therefore, includes a conditional check to determine if the ratio of the intermediate RV between the first and second bracket RVs is below some acceptable error threshold, as compared to the ratio of the intermediate calibration signal between the first and second bracket calibration signals. If the check is within the threshold, then method 500 continues to a wait state 516, after which the method 500 can recommence with step 502 to create another known calibration signal (e.g., before each octane/cetane test is run). For example, the user, or an automated control, can cause a repeat of the signal selection and re-initiation of signals associated with different values of octane or cetane number as is needed to calibrate the system, thereby providing scaling, stepping or varying of the output of the calibrator 202. Scaling can be achieved, for example, either by the generator 300 outputting different selectable amplitudes, or by the inducer 400 applying different magnetic fields so as to cause respective different output amplitudes from the pickup 102. If, however, the step 514 error exceeds a threshold, either at an instantaneous time or over a duration of the response signal, then the method 500 continues from step 514 to step 518.

Step 518 indicates a response to a threshold-exceeding detected error. For example, inasmuch as step 512 may display an image representation of the intermediate RV, step 518 may display a representation of, or information regarding, the error signal. The depiction of an error signal, or display of a value or ratio that does not match the expected ratio, demonstrates a possible faulty (including a noisy) connection or component in the path 106 or the operation or functionality of the DAS 100. Hence, each of those apparatus may be inspected or evaluated with additional processes and apparatus, so as to identify the location or cause of the imprecision. In addition, the DAS 100 may be re-calibrated (either manually or by a programmed or controlled automatic zeroing or biasing), taking into account the error for example as an offset, including a bias, so as to align a baseline DAS 100 output value back to match the expected value, thereby calibrating out a potential error in later output values or measurements once the generator 202 is disabled and the system is restored to, or used for, octane/cetane measurements. Alternatively or additionally, recall that feedback may be provided (see, e.g., FIG. 2) from the DAS to the calibrator 202; accordingly, detected error may be used as feedback to the calibrator 202, for example so that signal adjustments may be made into, or by, the calibrator 202 for future signal cycles. Accordingly, preferred embodiments permit calibrating, testing for bias, troubleshooting or biasing the DAS 100 in the use of acquiring, filtering, measuring and/or logging a signal responsive to the signal generated by the calibrator 202, and once the system is properly evaluated/corrected, coupling DAS 100 back to the pickup 102 for improved determination of octane or cetane numbers of fuels.

Figure 6:
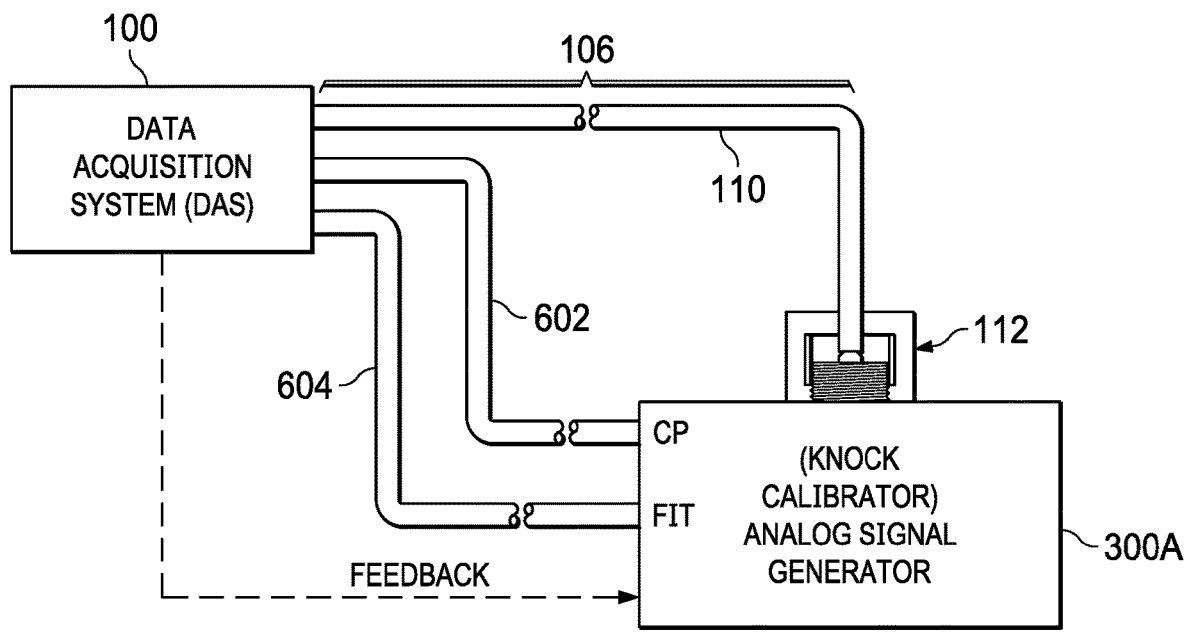
FIG. 6 repeats the illustration of FIG. 3, with the FIG. 3 generator modified to include additional functionality as may be used, for example, in connection with cetane measure calibration.
Figure 7:
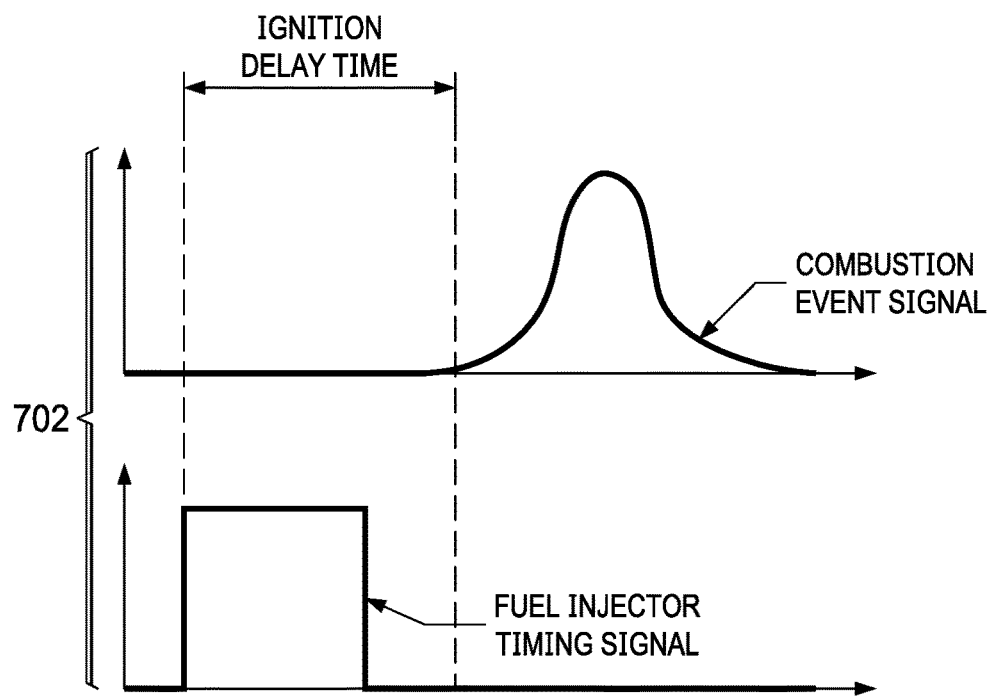
FIG. 7 illustrates timing diagram plots collectively depicting calibrator-supplied simulated combustion event signal following an ignition delay and operable duty cycle of a fuel injector.

FIG. 6 repeats the illustration of FIG. 3, with the generator 300 of FIG. 3 modified to include additional functionality and, therefore, for sake of reference indicated as generator 300A. Generator 300A may be particularly suitable, for example, in connection with calibrating a cetane-determining DAS. First, the generator 300A has a coupler (e.g., screw-on) 112 from which a combustion signal is provided. The combustion signal can be provided directly by signal generation such as from the embodiment of FIG. 3, or alternatively the signal may be an induced signal, for example sharing aspects from the embodiment of FIG. 4 with an inducer 400 inducing a simulated signal from a device (e.g., a testing pickup). Second, the generator 300A provides two additional outputs, connected to respective cables 602 and 604, representing additional simulated engine output signals to be received and processed by the DAS 100, that is, mimicking signals associated with an actual test engine 104, with it instead understood in FIG. 6 that the generator 300A is connected to the DAS 100 in lieu of connecting the DAS 100 to an actual test engine (or pickup 102 connected to that test engine). A first such signal is a crank position CP signal, representative of the rotational position (i.e., timing) of a test engine crankshaft, and correspondingly therefore likewise representative of any item mechanically connected to the crankshaft, including for example a piston reciprocating in the test engine cylinder or a flywheel. In an actual test engine environment, such a signal might typically be generated by a pickup according to a flywheel (or crankshaft connected thereto) associated with a test engine. A second such signal is a fuel injector timing FIT signal, representative of the duty cycle of operation of a fuel injector that would be coupled in an actual test, for example therefor as a pulse having a width equal to the time that the fuel injector is enabled to provide fuel to the engine cylinder. With the combined signaling of the generator 300A, the time delay of the associated generator output signal would be adjustable to mimic an actual ignition event on a running test engine, relative to timing from one or both of crankshaft position and fuel injector timing. The combination of signals are received by the DAS 100 to calculate the ignition delay associated with the start of the injector signal and the rising edge of the combustion signal, as seen in the timing diagram of FIG. 7. Specifically, FIG. 7 illustrates time along the horizontal axes of two plots 702 and signal amplitude along the vertical axes of those plots. The generator 300A may impose a simulated fuel injector timing signal as shown in the lower plot. The generator 300A also may impose an injected ignition delay time followed by a combustion event signal as shown in the upper plot, for example, to simulate a selected one of differing cetane valued fuels. In other words, in one instance, the generator 300A injects a first delay corresponding to a first cetane value, while in another instance, the generator 300A injects a second delay corresponding to a second cetane value, and so forth, for simulating different cetane fuel tests to DAS 100. With these additional attributes, simulated cetane measures may be determined again evaluating relative to bracket measures, where cetane measures evaluate the time delay between the turning on of the fuel injector and the start of the ignition event (which occurs from cylinder pressure), in relation to a crankshaft position. Accordingly, the calibrator 300A outputs a mimicked CP, then after some time a signal mimicking the fuel injector being enabled, and from that time to the simulated ignition/combustion event equates to the cetane measure.

Figure 8:
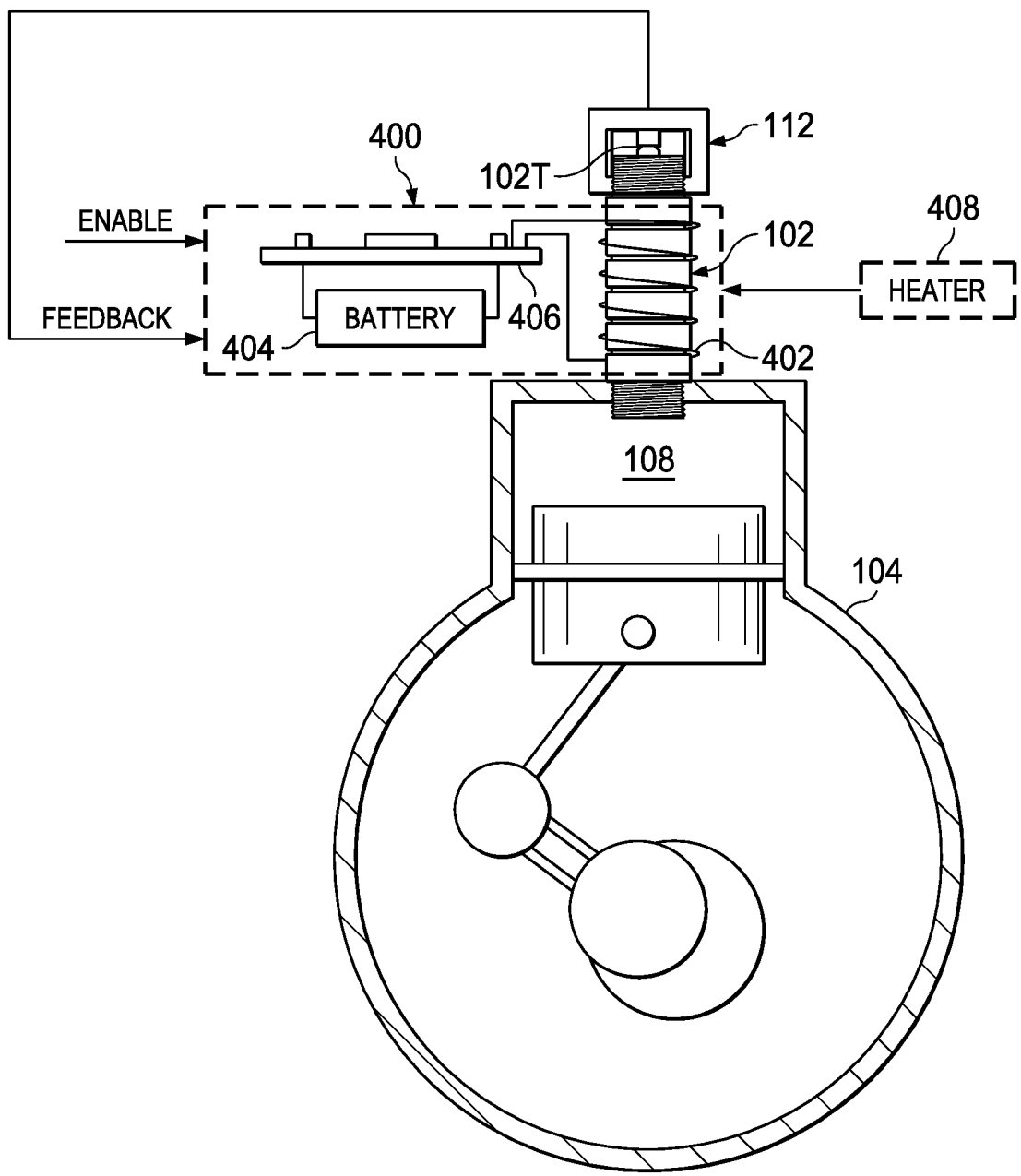
FIG. 8 illustrates a tuning setup for the FIG. 4 signal calibrator.

FIG. 8 illustrates a pre-calibration tuning setup for the calibrator of FIG. 4 (i.e., pickup signal inducer 400), for tuning that calibrator to ensure it will assuredly produce a mid-level amplitude signal to be communicated to the DAS 100, once the pickup 102 is reconnected to the cable 110 as shown in FIG. 4. As shown in FIG. 8, the pickup terminal(s) 102T provide a feedback signal back to the pickup signal inducer 400. In this manner, the inducer 400 is enabled and a pickup output is generated, and the feedback thereby facilitates a calibrator tuning process, whereby the stimulus generated by the inducer 400 may be adjusted. Such a process may be useful, since it will be assumed that different ones of individual pickups 102 will have slight variances of output signals in response to the energy of the calibrator's inducer 400. It is also assumed that the pickup output variances will not be linear in reference to a linear change in calibrator inducing energy. The variances in pickup output can be detected through feedback and accounted for by sensing and recording the peak output and adjusting the energy of the calibrator's inducer 400 to achieve the desired amplitude signal at the pickup's output terminals 102T.

Given the preceding, one skilled in the art should appreciate that certain preferred embodiments are intended to facilitate calibration of an octane or cetane determining data acquisition system, including the signal chain to that system. Detonation/ignition calibrator embodiments are provided that are operable to produce signals that represent various levels of octane signal amplitude or cetane ignition delay time. Such variability may permit a user to calibrate a DAS, which requires the evaluation of multiple signal amplitudes or delay times that represent fuels with different values of octane or cetane number. Additionally, illustrated calibrator embodiments also may be used beyond calibration of the DAS, but also as part of the fuel testing process. For example, typical fuel testing runs the test engine, and during that time the pickup coupled to the running test engine is a signal source to the DAS, which determines octane or cetane from the pickup signals. Given the present inventive teachings, however, a preferred embodiment calibrator 202 may be periodically substituted for the pickup/running engine. For example, in a first period the test engine may be run with the calibrator recording the engine detonation events, and then in a second period those recorded (or induced) events may be connected to the DAS during octane/cetane testing, in lieu of the DAS receiving those signals from the combination of a pickup and running engine. During the second period, therefore, the running engine would not be required for the rest of the fuel testing run, such as in an ASTM 2885 fuel testing system. Various other embodiments, advantages and features of the inventive scope will become apparent to those skilled in the art from the accompanying disclosure and drawings, as well as from the following claims.

What is claimed is:

1. A fuel quality rating testing system, comprising:
   a data acquisition system, comprising:
      circuitry for receiving a time-varying signal from a pickup, the pickup for coupling to a test engine; and
      circuitry for determining a fuel rating in response to the time-varying signal;
   a communications path coupled to the fuel quality rating testing system; and
   a calibrator, coupled to the communications path, for outputting an alternative time-varying signal without requiring a running test engine to concurrently couple a signal to the calibrator, wherein the circuitry for receiving receives the alternative time-varying signal and the circuitry for determining determines a fuel rating in response to the alternative time-varying signal.

2. The fuel quality rating testing system of claim 1 wherein the alternative time-varying signal is associated with a respective expected fuel rating, and further comprising circuitry for determining an error if the determined fuel rating in response to the alternative time-varying signal differs by more than a threshold from the expected fuel rating.

3. The fuel quality rating testing system of claim 2 wherein the expected fuel rating is determined in response to a fractional relationship of an attribute of the alternative time-varying signal relative to a first bracket alternative time-varying signal and a second bracket alternative time-varying signal.

4. The fuel quality rating testing system of claim 2 and further comprising circuitry for calibrating the data acquisition system in response to the error.

5. The fuel quality rating testing system of claim 4 wherein the calibrating adjusts the data acquisition system using the error as an offset for the data acquisition system to provide the expected fuel rating as the determined fuel rating in response to the alternative time-varying signal.

6. The fuel quality rating testing system of claim 2 and further comprising circuitry for calibrating the calibrator in response to the error.

7. The fuel quality rating testing system of claim 1 wherein the fuel rating is one of octane or cetane.

8. The fuel quality rating testing system of claim 1 wherein the calibrator comprises a signal generator for providing the alternative time-varying signal.

9. The fuel quality rating testing system of claim 8 wherein the signal generator is not connected to the test engine.

10. The fuel quality rating testing system of claim 8 wherein the signal generator further comprises circuitry for providing a crankshaft positioning indication.

11. The fuel quality rating testing system of claim 10 wherein the circuitry for determining determines a fuel rating in response to the alternative time-varying signal and the crankshaft positioning indication.

12. The fuel quality rating testing system of claim 10 wherein the signal generator delays an indicated combustion event as part of the alternative time-varying signal to simulate a selected one of differing cetane valued fuels.

13. The fuel quality rating testing system of claim 8 wherein the signal generator further comprises circuitry for providing a fuel injector timing signal.

14. The fuel quality rating testing system of claim 13 wherein the circuitry for determining determines a fuel rating in response to the alternative time-varying signal and the fuel injector timing signal.

15. The fuel quality rating testing system of claim 8 wherein the signal generator further comprises:
   circuitry for providing a crankshaft positioning indication; and
   circuitry for providing a fuel injector timing signal.

16. The fuel quality rating testing system of claim 15 wherein the circuitry for determining determines a fuel rating in response to the alternative time-varying signal, the crankshaft positioning indication, and the fuel injector timing signal.

17. The fuel quality rating testing system of claim 1 wherein the calibrator comprises:
   the pickup; and
   apparatus for applying a magnetic field proximate the pickup, wherein the pickup produces the alternative time-varying signal in response to the magnetic field.

18. The fuel quality rating testing system of claim 17 wherein the apparatus for applying is for applying magnetic fields of different magnitude at different times proximate the pickup.

19. The fuel quality rating testing system of claim 17 wherein the apparatus for applying a magnetic field comprises structure for positioning an induction coil around at least a portion of the pickup.

20. The fuel quality rating testing system of claim 17 and further comprising heating apparatus for transferring heat to the pickup.

21. The fuel quality rating testing system of claim 17 and further comprising heating apparatus, comprising a coil, for transferring heat to the pickup.

22. A method of calibrating a fuel quality rating testing system, the system comprising (i) circuitry for receiving a time-varying signal from a pickup, the pickup for coupling to a test engine, and (ii) circuitry for determining a fuel rating in response to the time-varying signal, the method comprising:

coupling a calibrator to a communications path;
coupling the communications path to the circuitry for receiving a time-varying signal from a pickup;
operating the calibrator to output an alternative time-varying signal, without requiring a running test engine to concurrently couple a signal to the calibrator;
receiving the alternative time-varying signal at the fuel quality rating system; and
operating the circuitry for determining to determine a fuel rating in response to the alternative time-varying signal.

23. The method of claim 22 wherein the alternative time-varying signal is associated with a respective expected fuel rating, and further comprising determining an error if the determined fuel rating in response to the alternative time-varying signal differs by more than a threshold from the expected fuel rating.

24. The method of claim 23 wherein the expected fuel rating is determined in response to a fractional relationship of an attribute of the alternative time-varying signal relative to a first bracket alternative time-varying signal and a second bracket alternative time-varying signal.

* * * * *